United States Patent [19]

Funk et al.

[11] 4,215,225

[45] Jul. 29, 1980

[54] PROCESS FOR PREPARING AMMONIUM SALTS OF ALKANOIC ACIDS

[75] Inventors: Andrew B. Funk; Max B. Williams, both of Memphis, Tenn.

[73] Assignee: W. R. Grace & Co., New York, N.Y.

[21] Appl. No.: 929,080

[22] Filed: Jul. 28, 1978

Related U.S. Application Data

[63] Continuation of Ser. No. 745,840, Nov. 29, 1976, abandoned.

[51] Int. Cl.$^2$ .............................................. C07C 51/52
[52] U.S. Cl. ................................... 562/606; 260/404; 562/607; 562/609
[58] Field of Search ....................... 562/606, 607, 609; 260/404

[56] References Cited

U.S. PATENT DOCUMENTS

| | | | |
|---|---|---|---|
| 3,488,386 | 1/1970 | Rice, Jr. | 562/608 |
| 3,579,297 | 5/1971 | Ekblom | 562/608 |
| 3,786,086 | 1/1974 | Skov et al. | 562/608 |
| 3,889,588 | 8/1975 | Skov et al. | 424/317 |

OTHER PUBLICATIONS

Zuffanti, J. A. Chem. Soc., 1941, 63, 3123-3124.

*Primary Examiner*—Vivian Garner
*Attorney, Agent, or Firm*—Elton Fisher; Philip M. Pippenger; Edward J. Cabic

[57] ABSTRACT

An ammonium salt of an alkanoic acid having about 1–10 carbon atoms per molecule is prepared by reacting ammonia with an excess of the alkanoic acid in an aqueous system in a tubular reactor.

An ammonium salt of an alkanoic acid having about 12–18 carbon atoms per molecule is prepared by reacting ammonia with the alkanoic acid in a tubular reactor. The reaction can be conducted in the presence or absence of water.

7 Claims, 4 Drawing Figures

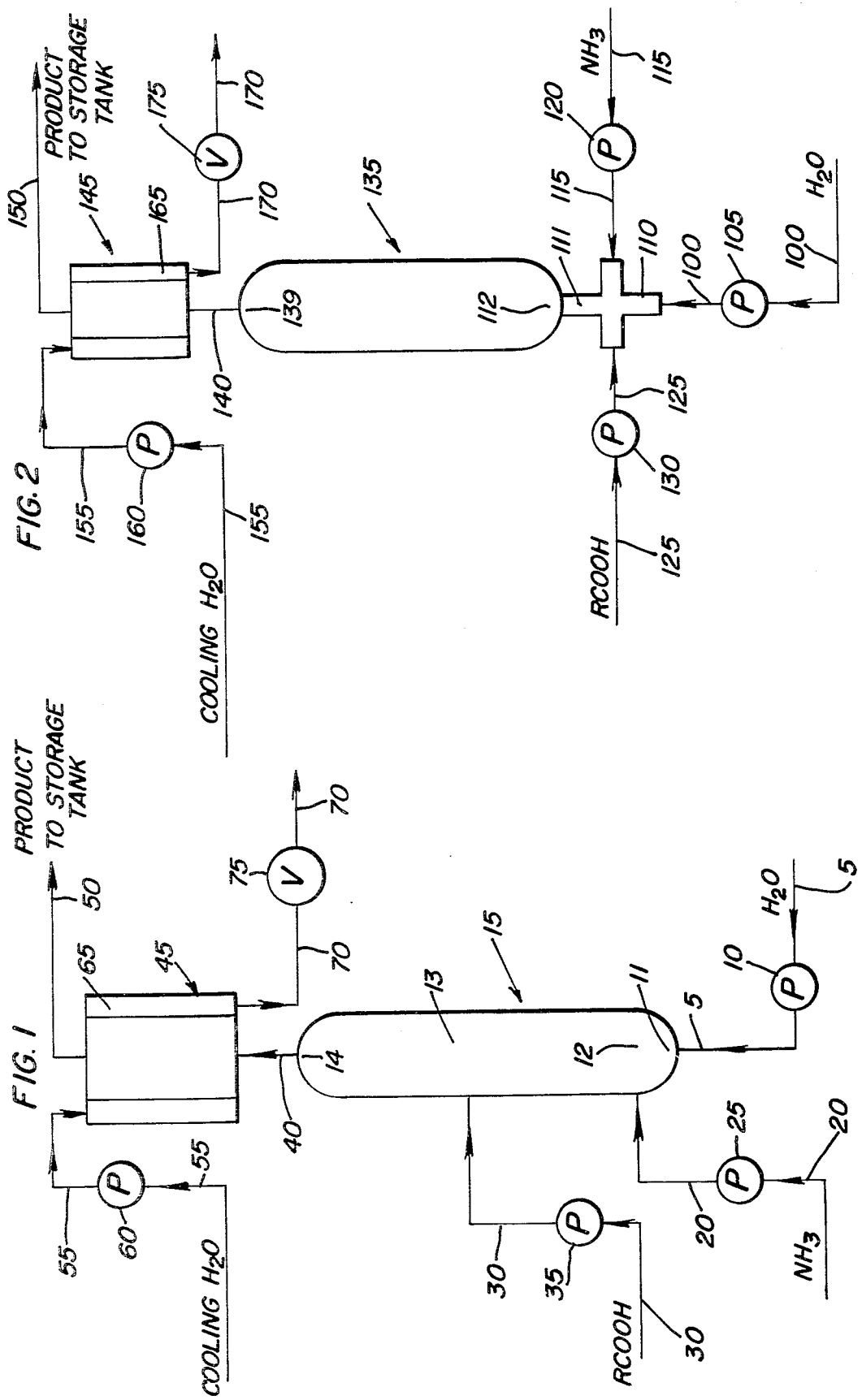

PROCESS FOR PREPARING AMMONIUM SALTS OF ALKANOIC ACIDS

This is a continuation of application Ser. No. 745,840, filed Nov. 29, 1976, now abandoned.

BACKGROUND OF THE INVENTION

This invention is in the field of ammonium salts of alkanoic acids. More particularly, this invention is in the field of preparing such salts. Still more particularly, this invention is directed to the use of a tubular reactor to prepare such salts.

Zuffanti, J. Am. Chem. Soc., 1941, 63, 3123–3124 teaches a method for preparing an ammonium salt of an alkanoic acid.

The preparation of such salt is also taught by U.S. Pat. Nos. 3,786,086 (Skov et al, 260/540) and No. 3,899,588 (Skov et al, 424/317).

U.S. Pat. Nos. 3,958,009 (Lapore et al, 424/317) and 3,806,600 (Lapore et al, 324/317) teach uses of ammonium and other salts of alkanoic acids. The above mentioned U.S. Pat. Nos. 3,786,086 and 3,898,588 also teach uses for ammonium salts of alkanoic acids.

SUMMARY OF THE INVENTION

In summary this invention is directed to an improvement in a process for preparing an ammonium alkanoate by reacting, in an aqueous medium, ammonia and an alkanoic acid having about 1–10 carbon atoms per molecule, the improvement comprising continuously:
(a) feeding a first admixture comprising water, ammonia, and an excess of the alkanoic acid into a tubular reaction zone;
(b) forming a second admixture comprising an aqueous solution of the ammonium alkanoate and unreacted alkanoic acid by passing the first admixture through the tubular reaction zone at a temperature effective for forming the ammonium alkanoate, said temperature being above the crystallization temperature of the second admixture;
(c) passing the second admixture exiting the tubular reaction zone through a tubular cooling zone and cooling the second admixture to a temperature effective for substantially eliminating ammonia vapor pressure over the second admixture, said temperature being above the crystallization temperature of the second admixture; and
(d) recovering the cooled second admixture.

BRIEF DESCRIPTION OF THE DRAWINGS

FIG. 1 is a schematic diagram of a vertical tubular reactor useful for preparing an ammonium alkanoate.

FIG. 2 is a schematic diagram of a vertical tubular reactor useful for preparing an ammonium alkanoate.

DESCRIPTION OF PREFERRED EMBODIMENTS

Figure 3:
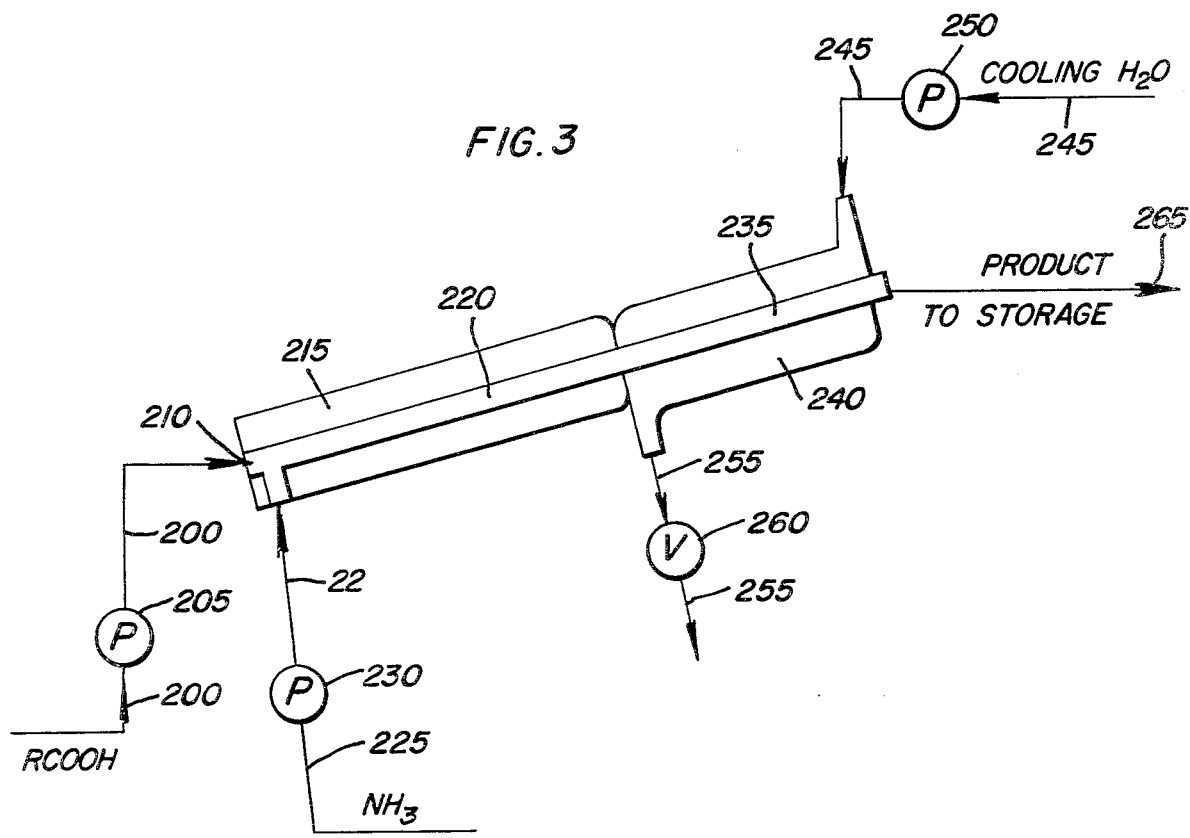
FIG. 3 is a schematic diagram of an inclined tubular reactor useful for preparing an ammonium alkanoate.

In preferred embodiments of this invention as recited in the above Summary:
1. The mole ratio of ammonia to alkanoic acid to water in the first admixture is 1–1.36:1.12–1.70:3.54–6.61.
2. The alkanoic acid is isobutyric acid.
3. The first admixture is formed by admixing the ammonia, the alkanoic acid, and water in a mixing cross, the mixing cross:
   (a) communicating with the tubular reaction zone; and
   (b) comprising an inlet port of the tubular reaction zone.
4. The ammonia and water are admixed in a mixing Tee and fed from the mixing Tee into the tubular reaction zone, the mixing Tee:
   (a) communicating with the tubular reaction zone; and
   (b) comprising a port of the tubular reaction zone;
   the alkanoic acid can be fed into the tubular reaction zone via a second inlet port positioned downstream of the first inlet port.

In another preferred embodiment ("Embodiment A") this invention is directed to an improvement in a process for preparing an aqueous solution of an ammonium alkanoate by reacting, in an aqueous medium, ammonia and an alkanoic acid having about 1–10 carbon atoms per molecule, the improvement comprising continuously:
(a) forming a first admixture comprising water, the ammonia, and an excess of the alkanoic acid in a vertical tubular reaction zone having: (i) a first lower portion; (ii) a second lower portion positioned above the first lower portion; (iii) a middle portion positioned above the second lower portion; and (iv) an upper portion positioned above the middle portion by feeding:
   (A) the water into said reaction zone via a water inlet port positioned in the first lower portion of said reaction zone;
   (B) the ammonia into said reaction zone via an ammonia inlet port positioned in the second lower portion of said reaction zone; and
   (C) the alkanoic acid into said reaction zone via an alkanoic acid inlet port positioned in the middle portion of said reaction zone, the water, anhydrous ammonia, and alkanoic acid being fed into said reaction zone at rates effective for preventing the alkanoic acid from descending into the second lower portion of said elongated vertical reaction zone;
(b) forming a second admixture comprising an aqueous solution of the ammonium alkanoate and unreacted alkanoic acid by passing the first admixture through the tubular reaction zone at a temperature effective for forming the ammonium alkanoate, said temperature being above the crystallization temperature of the second admixture;
(c) removing the second admixture from the upper portion of the reaction zone;
(d) passing the second admixture through a tubular cooling zone to cool the second admixture to a temperature effective for substantially eliminating ammonia vapor pressure over the second admixture, said temperature being above the crystallization temperature of the second admixture; and
(e) recovering the cooled second admixture.

In the process of this invention as recited in Embodiment A:
1. The mole ratio of ammonia to alkanoic acid to water in the first admixture can be 1–1.36:1.12–1.70:3.54–6.61.
2. The alkanoic acid can be isobutyric acid.

In another preferred embodiment ("Embodiment B") this invention is directed to an improvement in a process for preparing an ammonium alkanoate by reacting ammonia and an alkanoic acid having about 12-18 carbon atoms per molecule, the improvement comprising continuously:
(a) feeding a first admixture comprising water, ammonia, and the alkanoic acid all to total 100 percent, the alkanoic acid being present in an amount in excess of that required by the stoichiometry, into a tubular reaction zone;
(b) forming a second admixture comprising the ammonium alkanoate and unreacted alkanoic acid by passing the first admixture through the tubular reaction zone at a temperature effective for forming the ammonium alkanoate, said temperature being above the solidification temperature of the second admixture;
(c) passing the second admixture exiting the tubular reaction zone through a tubular cooling zone and cooling the second admixture to a temperature effective for substantially eliminating ammonia vapor pressure over the second admixture, said temperature being above the solidification temperature of the second admixture; and
(d) recovering the cooled second admixture.

In the process of this invention as recited in Embodiment B the alkanoic acid can preferably be stearic acid, palmitic acid, or lauric acid.

In another preferred embodiment ("Embodiment C") this invention is directed to an improvement in a process for preparing an ammonium alkanoate by reacting ammonia and an alkanoic acid having about 12-18 carbon atoms per molecule, the improvement comprising continuously:
(a) feeding a first admixture comprising water, ammonia, and the alkanoic acid, all to total 100 percent, with the alkanoic acid and the ammonia being present in stoichiometric amounts, into a tubular reaction zone;
(b) forming the ammonium alkanoate by passing the first admixture through the tubular reaction zone at a temperature effective for forming the ammonium alkanoate, said temperature being above the solidification temperature of the ammonium alkanoate;
(c) passing the ammonium alkanoate exiting the tubular reaction zone through a tubular cooling zone and cooling the ammonium alkanoate to a temperature effective for substantially eliminating ammonia vapor pressure over the second admixture, said temperature being above the solidification temperature of the ammonium alkanoate; and
(d) recovering the cooled second admixture.

In the process of this invention as recited in Embodiment C the acid can preferably be stearic acid, palmitic acid, or lauric acid.

DETAILED DESCRIPTION OF THE INVENTION

As noted supra, this invention is directed to a process wherein an ammonium alkanoate is prepared by passing an admixture comprising an alkanoic acid and ammonia through a tubular reaction zone (tubular reactor). Residence time in the tubular reactor is generally about 10-25 seconds but it can be less than 10 seconds and more than 25 seconds. The feedstock generally enters the reaction zone at about 60°-140° F., but this temperature range is not critical. The product generally exits the reaction zone at about 160°-260° F., but this temperature range is not critical. Product exiting the reaction zone is generally cooled to about 100°-180° F. in a tubular cooling zone (tubular cooler). However, this temperature range is not critical. If product exiting the reactor zone is within this range (ca. 100°-180° F.) the cooling step can be omitted.

The tubular reactor (tubular reaction zone) used in the process of this invention can be a vertical reactor, a horizontal reactor, or an inclined reactor. The tube comprising the reactor can be a straight tube, a curved tube, or a spiral tube. The tube can be insulated and/or jacketed to receive heat from a heating fluid (e.g., water, steam or the like) or to provide cooling (if required) from a cooling fluid such as water, oil or the like.

The cooling zone can preferably be a jacketed extension of the tubular reactor having a separate jacket (if the tubular reactor is jacketed) through which a cooling fluid can be circulated. Alternatively the cooling zone can be a tank which is jacketed to provide cooling or a tank with cooling coils therein.

Mixing the ammonia and the alkanoic acid with each other (and with water in those embodiments where an aqueous medium is used) to form a reaction mixture to pass through the tubular reactor can be accomplished via an inline mixer such as a mixing cross, one or more mixing Tees, one or more mixing Y's, or the like.

Alternatively, the water (where using an aqueous medium) can be fed into the tubular reactor at, or near one end (the inlet end), ammonia can be fed into the tubular reactor a short distance (e.g., 1-20 cm) downstream of the water inlet, and the alkanoic acid can be fed into the tubular reactor a short distance (e.g., 10-20 cm or more) downstream of the ammonia inlet. Where not using water, ammonia can be fed into the tubular reactor at or near the inlet end.

Where using one or more inline mixers, such mixers can, if desired, be insulated or jacketed to provide heating or cooling.

It will be readily apparent to those skilled in the art that the reactants (plus water where using an aqueous reaction medium) can be premixed to form a reaction mixture which can be kept in a storage zone (e.g., a tank) maintained at a temperature above the crystallization temperature (or solidification temperature) of the reaction mixture. Said reaction mixture can be pumped (or passed by gravity-induced flow) through the tubular reactor and subsequent cooling zone. No particular advantage is gained by using this technique.

Where using a vertical tubular reaction zone having a first lower portion, a second lower portion, a middle portion, and an upper portion the first lower portion of such vertical tubular reaction zone (vertical tubular reactor) which also has a bottom and a top can extend upward from the bottom of said tubular reaction zone to include about 1/20 to 1/10 of total height thereof. The second lower portion of said vertical tubular reaction zone can extend upward from immediately above the first lower portion of said reaction zone for about 1/5 to ⅓ of the total height thereof. The middle portion of the vertical tubular reaction zone can extend upward from immediately above the second lower portion of said reaction zone for about ⅛ to ½ of the total height thereof, and the upper portion of said tubular reaction zone comprises the remainder thereof (i.e., that portion of the said reaction zone which is above the middle portion).

It will also be readily apparent to those skilled in the art that at least part of the ammonia and water can be provided as an aqueous ammonia solution in those embodiments which use an aqueous medium. However, we generally prefer to use anhydrous liquid ammonia as our ammonia source and water per se as our water source.

It is preferred that flow rates but such as to maintain turbulent flow through the tubular reaction zone and the tubular cooling zone.

The mole ratios of the reactants (and water) recited in certain of the above embodiments are important but not critical. However, where using the methods of this invention as recited in the Summary and in Embodiments A and B, it is very important that an excess of the alkanoic acid over that required by the stoichiometry be used. Where using the method of this invention recited in Embodiment C it is very important that stoichiometric amounts of ammonia and alkanoic acid be used.

Referring to FIG. 1: Water enters the first lower portion 11 of the vertical reactor (vertical reaction zone) shown generally at 15 via line 5 and pump 10. Ammonia enters the second lower portion 12 of said vertical reactor via line 20 and pump 25. The alkanoic acid (RCOOH) enters the middle portion 13 of said vertical reactor via line 30 and pump 35. The product exits from the top 14 of said vertical reactor via line 40 and passes into the cooling zone shown generally at 45. Cooling water enters jacket 65 of said cooling zone via line 55 and pump 60. The cooling water exits jacket 65 via line 70 and regulatory valve 75 which is used to restrict the rate of flow of the cooling water through the jacket. While the drawing shows countercurrent flow of the cooling water, concurrent flow is operable. Cooled product exits said cooling zone via line 50 and passes to a product storage tank (not shown).

Referring to FIG. 2: Water enters mixing cross 110 via line 100 and pump 105. Ammonia enters said mixing cross via line 115 and pump 120. The alkanoic acid (RCOOH) enters said mixing cross via line 125 and pump 130. The resulting admixture produced by admixing water, ammonia, and alkanoic acid in mixing cross 110 passes via arm 111 of said mixing cross into lower portion 112 of the vertical reactor shown generally at 135. Product formed in said vertical reactor passes from upper portion 139 of said vertical reactor via line 140 into the cooling zone shown generally at 145. Cooling water enters jacket 165 of said cooling zone via line 155 and pump 160 and exits jacket 165 via line 170 and regulatory valve 175 which is used to restrict the rate of flow of the cooling water. While the drawing shows countercurrent flow of the cooling water, concurrent flow is operable. Cooled product exits said cooling zone via line 150 and passes to a product storage tank (not shown).

Referring to FIG. 3: Alkanoic acid (RCOOH) enters mixing Tee 210 [which is an integral part of inclined reactor (inclined reaction zone) 220] via line 200 and pump 205. Ammonia enters mixing Tee 210 via line 225 and pump 230. Insulation 215 covers both inclined reactor 220 and mixing Tee 210. The admixture of alkanoic acid and ammonia formed in mixing Tee 210 passes through inclined reactor 220 and into a cooler or cooling zone 235 [which is a continuation of inclined reactor 220 with jacket 240 (in place of insulation) surrounding it]. Cooling water passes into jacket 240 via line 245 and pump 250. The cooling water exits jacket 240 via line 255 and regulatory valve 260. Although the drawing shows countercurrent flow of the cooling water, concurrent flow is operable. Cooled product exit cooling zone 235 passes via line 265 to a product storage tank (not shown).

Figure 4:
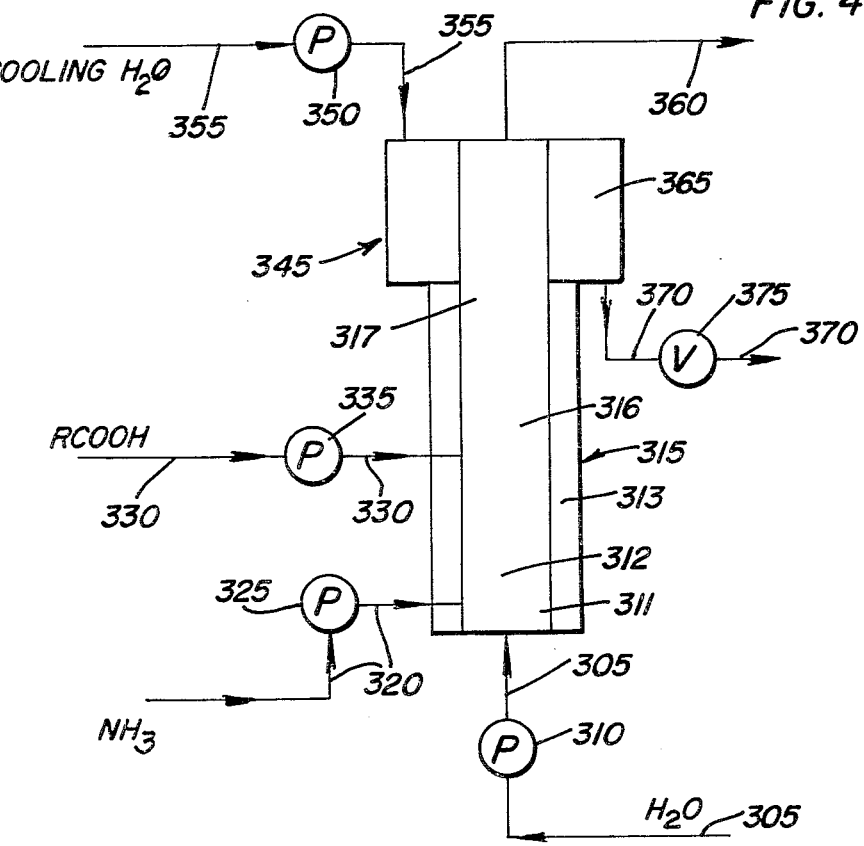
FIG. 4 is a schematic diagram of a vertical tubular reactor useful for preparing an ammonium alkanoate.

Referring to FIG. 4: Water enters first lower portion 311 of the vertical reactor (vertical reaction zone) shown generally at 315 via line 305 and pump 310. Ammonia enters second lower portion 312 of said vertical tubular reactor via line 320 and pump 325. Alkanoic acid (RCOOH) enters middle portion 316 of said vertical tubular reactor via line 330 and pump 335. Insulation 313 covers said vertical tubular reactor. Product leaves upper portion 317 of said vertical reactor and passes into the cooling zone shown generally at 345 (which is a continuation of said vertical tubular reactor with jacket 365 (in place of insulation) surrounding it). Cooling water passes into jacket 365 via line 355 and pump 350. The cooling water exits jacket 365 via line 370 and regulatory valve 375. Cooled product exits said cooler via line 360 and passes to a product storage tank (not shown).

The instant invention will be better understood by referring to the following specific but nonlimiting examples. It is understood that said invention is not limited by these examples which are offered merely as illustrations; it is also understood that modifications can be made without departing from the spirit and scope of the invention.

The examples were actually run.

EXAMPLE 1

The run of this example was made using an apparatus of the type represented by FIG. 1 except that the vertical tubular reactor (shown generally at 15) and the cooling zone (shown generally at 45) were insulated with a magnesia insulating composition.

Water was continuously charged into first lower portion 11 of a vertical tubular reactor (vertical tubular reaction zone) shown generally at 15 via line 5. Liquid anhydrous ammonia was continuously charged into second lower portion 12 of said vertical tubular reactor via line 20, and isobutyric acid was continuously charged into middle portion 16 of said vertical tubular reactor via line 30. Product (as aqueous solution comprising water, ammonium isobutyrate, and unreacted excess isobutyric acid) continuously passed from upper portion 14 of said vertical reactor into the jacketed cooling zone shown generally at 45. Cooled product continuously passes from said cooling zone via line 50 to a product receiver. Cooling water continuously passed through jacket 65 which surrounded cooling zone.

Flow rates were:

| Material | Grams per Minute |
| --- | --- |
| Water | 29.5 |
| Ammonia | 6.1 |
| Isobutyric Acid | 36.0 |

Water and isobutyric acid were charged into the vertical tubular reactor at about 75° F. and the ammonia was charged into said reactor at a pressure of 6 pounds per square inch (6 psig).

Linear velocity in the vertical tubular reactor was 4.74 feet per minute and residence time in said reactor was 11.6 seconds.

The temperature of the ammonia-water mixture (aqua ammonia) just below the middle portion of the vertical tubular reactor was 152° F., the temperature of the product exiting the vertical tubular reactor (i.e., just before entering the cooler (cooling zone)) was 235° F., and the temperature of the product exiting the cooler 45 was 156° F.

Conversion (one pass yield) was substantially complete (i.e., 100% of theory).

EXAMPLE 2

The general method of Example 1 was repeated. In this instance flow rates were:

| Material | Grams per Minute |
|---|---|
| Water | 40.8 |
| Ammonia | 9.2 |
| Isobutyric Acid | 50.1 |

The water and isobutyric acid were charged into the vertical tubular reaction zone at about 75° F., and ammonia was charged into said reaction zone at a pressure of 6 psig. Linear velocity in the vertical tubular reactor was 6.6 feet per minute and residence time was 8.4 seconds.

The temperature of the ammonia-water mixture (aqua ammonia) just below the middle portion of the vertical tubular reaction zone was 148° F., the temperature of the product exit the vertical tubular reaction zone was 228° F., and the temperature of the product exit the cooler was 164° F.

Conversion was substantially complete.

EXAMPLE 3

The general method of Example 1 was repeated. In this instance the method was modified by replacing the isobutyric acid with pelargonic acid.

In this instance feed rates (input rates) were:

| Material | Grams per Minute |
|---|---|
| Water | 27.1 |
| Ammonia | 7.7 |
| Pelargonic Acid | 24.9 |

The water and pelargonic acid were charged into the vertical tubular reaction zone at 75° F., and the ammonia was charged into said reaction zone at a pressure of 6 psig. The temperature of the ammonia-water mixture (aqua ammonia) just below the middle portion of the vertical tubular reaction zone was 155° F., the temperature of the product exiting the vertical tubular reaction zone was 175° F., and the temperature of the product exiting the cooler was 138° F.

Conversion was substantially complete.

EXAMPLE 4

The general method of Example 1 was repeated. In this instance the method was modified by replacing the isobutyric acid with caprylic acid.

In this instance the feed rates (input rates) were:

| Material | Grams per Minute |
|---|---|
| Water | 30.1 |
| Ammonia | 10.4 |
| Caprylic Acid | 42.5 |

The water and caprylic acid were charged into the vertical tubular reaction zone at 75° F. and the ammonia was charged into said reaction zone at a pressure of 6 psig.

The temperature of the ammonia-water mixture (aqua ammonia) just below the middle portion of the vertical tubular reaction zone was 154° F., the temperature of the product exiting the vertical tubular reaction zone was 186° F., and the temperature of the product exiting the cooler was 122° F.

Conversion was substantially complete.

The ammonium alkanoates of this invention are useful for preventing rot and mildew from forming on silage, seeds, hay, and the like.

The above mentioned U.S. Pat. Nos. 3,958,009, 3,806,600, 3,786,086, and 3,898,588 which, as noted supra, teach uses for ammonium alkanoates, are incorporated herein by reference in their entirities.

We claim:

1. In a process for preparing an ammonium alkanoate by reacting, in an aqueous medium ammonia and an alkanoic acid having about 1–10 carbon atoms per molecule, the improvement comprising continuously:
   (a) feeding a first admixture comprising water, ammonia, and an excess of the alkanoic acid into a tubular reaction zone,
   (b) forming a second admixture comprising an aqueous solution of the ammonium alkanoate and unreacted alkanoic acid by passing the first admixture through the tubular reaction zone, said first admixture having a temperature of from about 60° to 140° F. as it enters said reaction zone, said second admixture having a temperature of from about 160° to 260° F. at the exit end of said reaction zone;
   (c) passing the second admixture exiting the tubular reaction zone through a tubular cooling zone and cooling the second admixture to a temperature of from about 100° to 180° F.; and
   (d) recovering the cooled second admixture.

2. The process of claim 1 in which the first admixture is formed by admixing the ammonia, the alkanoic acid, and water in a mixing cross, the mixing cross:
   (a) communicating with the tubular reaction zone; and
   (b) comprising an inlet port of the tubular reaction zone.

3. In a process for preparing an aqueous solution of an ammonium alkanoate by reacting, in an aqueous medium, ammonia and an alkanoic acid having about 1–10 carbon atoms per molecule, the improvement comprising continuously:
   (a) forming a first admixture comprising water, the ammonia, and an excess of the alkanoic acid in a vertical tubular reaction zone having: (i) a first lower portion; (ii) a second lower portion positioned above the first lower portion; (iii) a middle portion positioned above the second lower portion; and (iv) an upper portion positioned above the middle portion by feeding:
      (A) the water into said reaction zone via a water inlet port positioned in the first lower portion of said reaction zone;
      (B) the ammonia into said reaction zone via an ammonia inlet port positioned in the second lower portion of said reaction zone; and
      (C) the alkanoic acid into said reaction zone via an alkanoic acid inlet port positioned in the middle portion of said reaction zone, the water, anhydrous ammonia, and alkanoic acid being fed into said reaction zone at rates effective for preventing the alkanoic acid from descending into the second lower portion of said vertical reaction zone;

(b) forming a second admixture comprising an aqueous solution of the ammonium alkanoate and unreacted alkanoic acid by passing the first admixture through the tubular reaction zone, said first admixture having a temperature of from about 60° to 140° F. as it enters said reaction zone, said second admixture having a temperature of from about 160° to 260° F. at the exit end of said reaction zone;

(c) removing the second admixture from the upper portion of the reaction zone;

(d) passing the second admixture through a tubular cooling zone to cool the second admixture to a temperature of from about 100° to 180° F.;

(e) recovering the cooled second admixture.

4. The process of claim 3 in which the mole ratio of ammonia to alkanoic acid to water in the first admixture is 1–1.36:1.12–1.70:3.54–6.61.

5. The process of claim 4 in which the alkanoic acid is isobutyric acid.

6. In a process for preparing an ammonium alkanoate by reacting, in an aqueous medium, ammonia and an alkanoic acid having about 1–10 carbon atoms per molecule, the improvement comprising continuously:

(a) forming a second admixture comprising an aqueous solution of the ammonium alkanoate and unreacted alkanoic acid by passing a first admixture comprising ammonia, the alkanoic acid, and water through the tubular reaction zone, said first admixture having a temperature of from about 60° to 140° F. as it enters said reaction zone, said second admixture having a temperature of from about 160° to 260° F. at the exit end of said reaction zone; the mole ratio of ammonia to alkanoic acid to water in the first admixture being 1–1.36:1.12–1.70:3.54–6.61;

(b) passing the second admixture exiting the tubular reaction zone through a tubular cooling zone and cooling the second admixture to a temperature of from about 100° to 180° F.; and (c) recovering the cooled second admixture.

7. The process of claim 6 in which the alkanoic acid is isobutyric acid.

* * * * *